United States Patent [19]

Ophir et al.

[11] Patent Number: 4,878,500
[45] Date of Patent: Nov. 7, 1989

[54] MULTI-BEAM TRACKING FOR ANGLE ERROR CORRECTION IN SPEED OF SOUND ESTIMATIONS

[75] Inventors: Jonathan Ophir; David P. Shattuck, both of Houston, Tex.

[73] Assignees: The University of Texas System, Austin; The University of Houston-University Park, Houston, both of Tex.

[21] Appl. No.: 218,810

[22] Filed: Jul. 13, 1988

Related U.S. Application Data

[63] Continuation-in-part of Ser. No. 887,349, Jul. 21, 1986, Pat. No. 4,807,635, and a continuation-in-part of Ser. No. 823,322, Jan. 28, 1986, Pat. No. 4,777,958, which is a continuation-in-part of Ser. No. 791,719, Oct. 28, 1985, Pat. No. 4,669,482.

[51] Int. Cl.[4] .................................................. A61B 8/00
[52] U.S. Cl. .................................. 128/660.01; 73/597; 73/602
[58] Field of Search ...................... 128/660.01, 660.07; 73/597, 602

[56] References Cited

U.S. PATENT DOCUMENTS

| | | | |
|---|---|---|---|
| 4,669,482 | 6/1987 | Ophir | 73/597 X |
| 4,700,571 | 10/1987 | Okazaki | 73/597 |
| 4,777,958 | 10/1988 | Ophir | 73/597 X |
| 4,781,199 | 11/1988 | Hirama et al. | 73/597 X |
| 4,807,635 | 2/1989 | Ophir | 73/602 X |

Primary Examiner—Francis Jaworski
Attorney, Agent, or Firm—Arnold, White & Durkee

[57] ABSTRACT

This invention relates to a method for correcting angle error present in in vivo sound velocity estimations. More particularly, this invention relates to a method for estimating the angle of misdirection of a tracked ultrasound beam used in sound velocity measurements in conjunction with multi-tracking ultrasound beams.

15 Claims, 4 Drawing Sheets

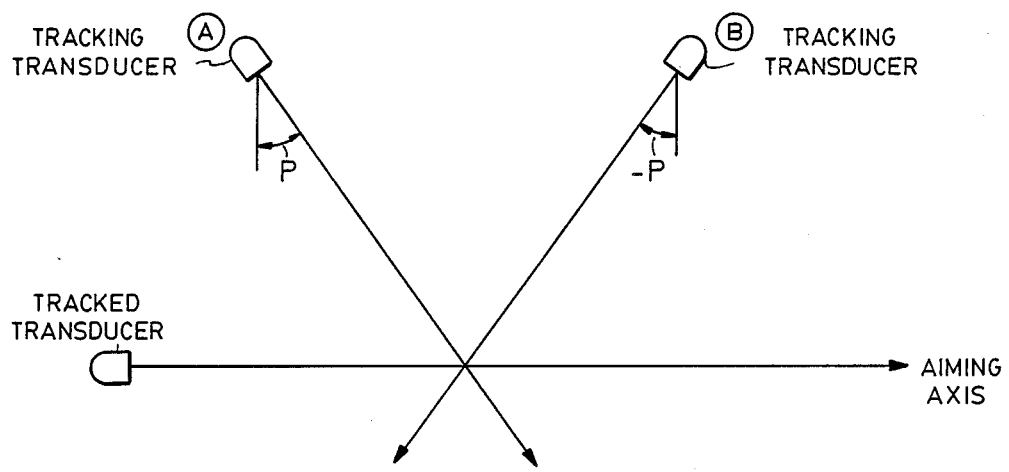
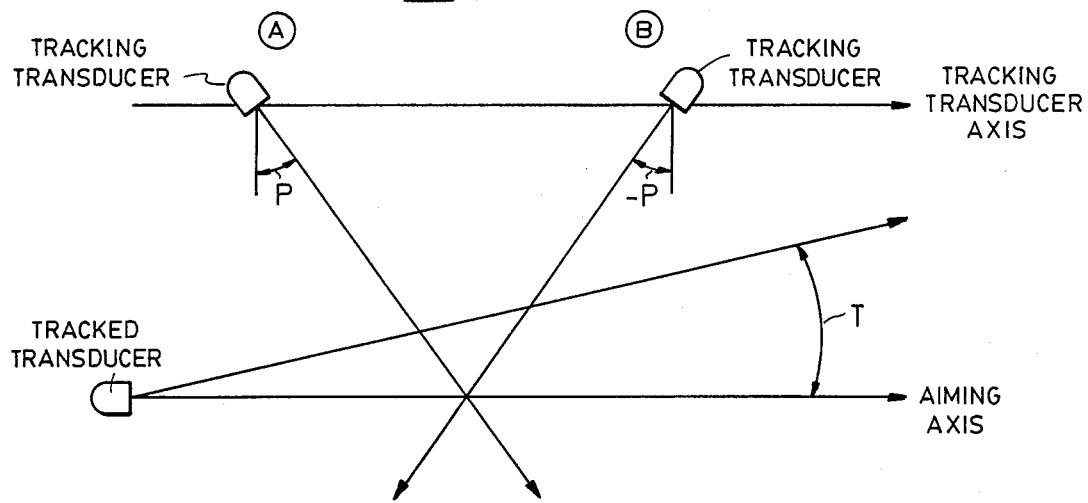

MULTI-BEAM TRACKING FOR ANGLE ERROR CORRECTION IN SPEED OF SOUND ESTIMATIONS

CROSS-REFERENCE TO RELATED APPLICATIONS

This application is a continuation-in-part of U.S. application Ser. No. 887,349, entitled, "Pulse Centroid Echo Method and Apparatus for Enhanced Sound Velocity Estimation in Vivo", filed July 21, 1986, and now U.S. Pat. No. 4,807,635 and a continuation-in-part of U.S. application Ser. No. 823,322, entitled, "Method for Enhancing the Accuracy of In Vivo Sound Velocity Estimation", filed Jan. 28, 1986, and now U.S. Pat. No. 4,779,958, which in turn is a continuation-in-part of U.S. application Ser. No. 791,719, filed Oct. 28, 1985 which issued as U.S. Pat. No. 4,669,482 on June 2, 1987. Applicant incorporates application Ser. Nos. 887,349, and 823,332 by reference herein and claims the benefit of said applications for all purposes pursuant to 37 C.F.R. § 1.78.

BACKGROUND OF THE INVENTION

1. Field of the Invention

This invention relates to a method for correcting angle induced error present in in vivo sound velocity estimations. More particularly, this invention relates to a method for estimating the angle of misdirection of a tracked ultrasound beam used in sound velocity measurements in conjunction with one or more tracking ultrasound beams.

2. Description of the Prior Art

Ultrasound techniques have been extensively used in the field of diagnostic medicine as a nontoxic means of analyzing the properties of in vivo (i.e., living) tissue. Ultrasound can be used for both tissue imaging as well as the measurement of the speed of sound in organic tissue. In particular, the speed of sound in an organ can be one indication of the presence of disease within that organ.

Tracked beam orientation is very important in obtaining accurate sound velocity measurements using beam tracking methods. A tracked beam may become misdirected for a variety of reasons, including improper transducer orientation, refraction, and improper phasing circuitry operation. Such misdirection produces an angle error in ultrasound velocity measurements.

In beam tracking methods used to determine in vivo sound velocity, such as those methods disclosed in U.S. Pat. No. 4,669,482 to Ophir, the misdirection of the tracked beam by an angle T introduces an error factor into the sound velocity estimate obtained by the method shown. This error factor is equal to $[1-\sin(T)]/\cos(T)$ where T is the angle of misdirection of the tracked beam.

SUMMARY OF THE INVENTION

This invention discloses a method for enhanced in vivo sound velocity estimations using multiple tracking transducers. The sound velocity estimations taken by the methods of the present invention are enhanced because the normal error resulting from misdirection of the tracked beam is corrected in determining sound velocity. Thus, the sound velocity estimations taken by the methods of the present invention do not contain an error factor which is a function of the angle of misdirection of the tracked beam.

In the beam tracking methods of the prior art for in vivo sound velocity estimation, transducers are oriented along the outer surface of the target medium and directed inward into the target. It is common in these methods for one of such transducers, known as a tracked transducer, to be oriented along an aiming axis extending through the target medium tissue. The tracked transducer emits a tracked ultrasound beam into the target medium, the tracked ultrasound beam is misdirected by an angle T from the aiming axis.

In conventional beam tracking methods, a multiplicity of tracking transducers may be oriented along parallel axes directed into the target area in a direction which is normal to the direction of the aiming axis. In lieu of multiple tracking transducers, multiple measurements may be taken by repositioning only one tracking transducer. The tracking transducers are aligned such that beams directed from the tracking transducers will intersect the ultrasound beam emitted from the tracked transducer. Such a beam tracking method allows one to estimate the velocity of sound along a segment of the tracked beam lying between the points of intersection with two parallel tracking beams by measuring the difference in time required for ultrasound energy to travel from the tracked transducer to each of the two tracking transducers which emit the two parallel tracking beams.

Based upon this principle, it is readily apparent that the misdirection of the tracked beam introduces an error factor into velocity estimations obtained by this method because the misdirected tracked beam will intersect each tracking beam at a point which is at a different distance from the tracking transducer which emits the tracking beam.

It will be shown later in this description that the magnitude of the error factor resulting from misdirection of the tracked beam is $[1-\sin(T)]/\cos(T)$. The practical difficulty posed by this error factor is that the angle T is not known. The present invention discloses a method for measuring T and correcting in vivo sound velocity estimations determined from beam tracking methods.

In the simplest form of the present invention, three tracking transducers and one tracked transducer are required. The tracked transducer is applied to the outer surface of the target medium oriented along an aiming axis. One of the tracking transducers is applied to the outer surface of the target medium along an axis normal to the aiming axis of the tracked transducer. This tracking transducer is known as the central tracking transducer.

The two remaining tracking transducers are applied to the outer surface of the target medium on opposite sides of the central tracking transducer to form a tracking transducer axis with the central tracking transducer. The tracking transducer axis is parallel to the aiming axis and lies in the same two dimensional plane as the aiming axis. The outer tracking transducer to the left of the central tracking transducer is oriented toward the central tracking transducer at an angle P from an axis normal to the aiming axis. The outer tracking transducer to the right of the central tracking transducer is oriented toward the central tracking transducer at an angle $-P$ from an axis normal to the aiming axis.

The outer tracking transducer may be oriented at angle P or $-P$, as described above, by physically aiming the body of the transducer along this angle and operating the transducer such that it receives or transmits ultrasound beams along the axis at which it is aimed. In an alternative embodiment, using phased arrays of transducers, the outer tracking transducers may be oriented at an angle P or −P, by operating the phased array circuitry to receive or transmit ultrasound beams at such a selected angle. In this embodiment, a multiplicity of tracking transducers can be placed on the target area, each of these tracking transducers physically oriented along an axis normal to the aiming axis. The phased array circuitry can then be used to direct or transmit ultrasound beams from a particular phased array of transducer elements at a desired angle, such as −P, P, or coincident with an axis normal to the aiming axis.

After proper transducer orientation is achieved, a tracked beam is generated from the tracked transducer. This beam is misdirected at an angle T from the aiming axis. Ultrasound energy is scattered from scatterers along the tracked beam to each of the tracking transducers.

The ultrasound transducers used in practicing the present invention are of a piezoelectric type well-known in the ultrasound art. The transducers contain a crystal of a material such as quartz or other suitable material exhibiting a piezoelectric effect. That is, when an electric signal voltage is applied across the crystal, the crystal will mechanically vibrate or oscillate responsive to the signal voltage. Conversely, when a mechanical vibration is applied to the crystal, a signal voltage will be present across the crystal responsive to the mechanical vibration. Transducers may therefore be used to either transmit or receive ultrasound energy.

In one method of the present invention, an ultrasound beam is emitted from the tracked transducer and scattered to each of the tracking transducers. Thus, the tracked transducer acts as a transmitting transducer and the tracking transducers act as receiving transducers. In another method of the present invention which works equally well, ultrasound beams are emitted from the tracking transducers and scattered to the tracked transducer.

Each of the transducers used to practice this invention is coupled to an energy measuring and timing device, such as an oscilloscope. The time required for ultrasound energy to travel from the tracked transducer to each of the tracking transducers is measured and recorded by the energy measuring and timing device. In one embodiment of the present invention, this data is stored in a computer for later analysis.

After this data is measured and recorded, all of the tracking transducers are relocated a distance $\Delta x$ from their present location in the same direction along the tracking transducer axis. The direction in which these transducers are relocated is known as the direction of translation. In one embodiment of the present invention, the three tracking transducers are fastened to an attachment arm so that movement of the attachment arm by a distance, $\Delta x$, results in movement of each of the tracking transducers by a distance $\Delta x$. A tracked beam is again generated by the tracked transducer and tracking beams which intersect the tracked beam are again received by the tracking transducers. The time required for ultrasound energy to travel from the tracked transducer to each of the tracking transducers is again measured and recorded. The tracking transducers are then moved a distance $\Delta x$ in the same direction as before and another set of measurements is taken. This procedure is repeated at each location for each of the tracking transducers.

In an alternative embodiment of the present invention, the body or target area is lined with a multiplicity of tracking transducers aligned along a tracking transducer axis which is parallel to the aiming axis. These tracking transducers are electronically coupled to a measuring and timing device via a switch mechanism. By manipulating the switch mechanism, three groups of tracking transducers can be selectively coupled to the measuring and timing device in order to obtain a multiplicity of data sets for locations separated by a distance $\Delta x$ moving along the tracking transducer axis. These groups of transducers may consist of single transducers or arrays of multiple transducer elements. This embodiment produces the equivalent result of physically relocating three tracking transducers by a distance $\Delta x$, as described above.

In another embodiment of the present invention, the tracking transducer configuration explained above is modified to use two pairs of tracking transducers instead of three tracking transducers as described in the above embodiment. One pair of tracking transducers consists of a left tracking transducer oriented at an angle P1 from an axis normal to the aiming axis and a right tracking transducer oriented at an angle −P1 from an axis normal to the aiming axis. The second pair of tracking transducers consists of a left transducer oriented at an angle P2 from an axis normal to the aiming axis and a right tracking transducer oriented at an angle −P2 from an axis normal to the aiming axis. The travel time for ultrasound energy to travel from the tracked transducer to each of the tracking transducers is measured and recorded as described above. After data sets are obtained for each pair of tracking transducers at their present location, the tracking transducers are translated along the tracking transducer axis a distance $\Delta x$ and another pair of data sets are obtained. This procedure is repeated to obtain a multiplicity of data sets.

From the recorded data for each tracking transducer at each location, a functional relationship is determined between travel time and location from the plurality of measured data sets. This functional relationship can be determined by plotting the times measured for each transducer as a function of its location.

The speed of sound along the tracked beam is determined from this functional relationship. One method of determining the speed is to use a linear regression technique to fit a line to the plurality of data sets obtained for each tracking transducer. The slope of the line can then be calculated to yield a velocity estimation.

As a final step, the speed of sound, C, is then determined. In the embodiment of the present invention which utilizes a central tracking transducer and two outer tracking transducers, the speed of sound, C, is found by solving the following two equations:

$$C = CE[1 - \sin(T)]/\cos(T); \text{ and}$$

$$\sin(T) \frac{\sin(2P) + \cos(T + P) - \cos(T - P)}{[\cos(T + P)][\cos(T - P)]} = \frac{C}{CB} - \frac{C}{CA}$$

where
CE = the speed of sound determined from the data pairs taken for the central tracking transducer;
T = the angle of misdirection which the tracked beam undergoes;

P = the angle between the axis along which the left outer tracking transducer is aimed and an axis normal to the aiming axis;

CA = the speed of sound determined from the data pairs taken for the left outer tracking transducers; and CB = the speed of sound determined from the data pairs taken for the right outer tracking transducer.

In the embodiment of the present invention which utilizes two pairs of tracking transducers, the speed of sound, C, is determined by solving the following two equations:

$$\sin(T)\frac{\sin(2P1) + \cos(T + P1) - \cos(T - P1)}{[\cos(T + P1)][\cos(T - P1)]} = \frac{C}{CB} - \frac{C}{CA}$$

$$\sin(T)\frac{\sin(2P2) + \cos(T + P2) - \cos(T - P2)}{[\cos(T + P2)][\cos(T - P2)]} = \frac{C}{CZ} - \frac{C}{CY}$$

where

CA = the speed of sound determined from the data pairs taken for the left tracking transducer oriented at angle P1;

CB = the speed of sound determined from the data pairs taken for the right tracking transducer oriented at angle $-P1$;

CZ = the speed of sound determined from the data pairs taken for the left tracking transducer oriented at angle P2; and CY = the speed of sound determined from the data pairs taken for the right tracking transducer oriented at angle $-P2$.

BRIEF DESCRIPTION OF THE DRAWINGS

FIG. 1 is a geometric representation of a beam tracking method in which no misdirection takes place.

FIG. 2 is a geometric representation of a beam tracking method in which misdirection takes place.

DESCRIPTION OF THE PREFERRED EMBODIMENTS

In the discussion which follows, the theoretical principles and mathematical derivations which support the validity of the methods of the present invention are described.

In a simple multi-beam tracking scenario, a tracked transducer oriented along an aiming axis emits a tracked beam which is intersected by two tracking beams. The tracking beams are emitted from a left and a right tracking transducer oriented at angles P and $-P$, respectively, from an axis normal to the aiming axis. As shown in FIG. 1, where the tracked beam undergoes no misdirection, the time required for ultrasound energy to travel from the tracked transducer to each tracking transducer is equal.

Referring to FIG. 2, we now assume that the tracked beam is misdirected at an angle T from the aiming axis. Ultrasound energy emitted from the tracked transducer will therefore travel to tracking transducer A in less time than it takes for similar ultrasound energy to travel to tracking transducer B. This observation is based upon the assumption that the speed of sound is uniform along the travel paths referenced.

Figure 3:
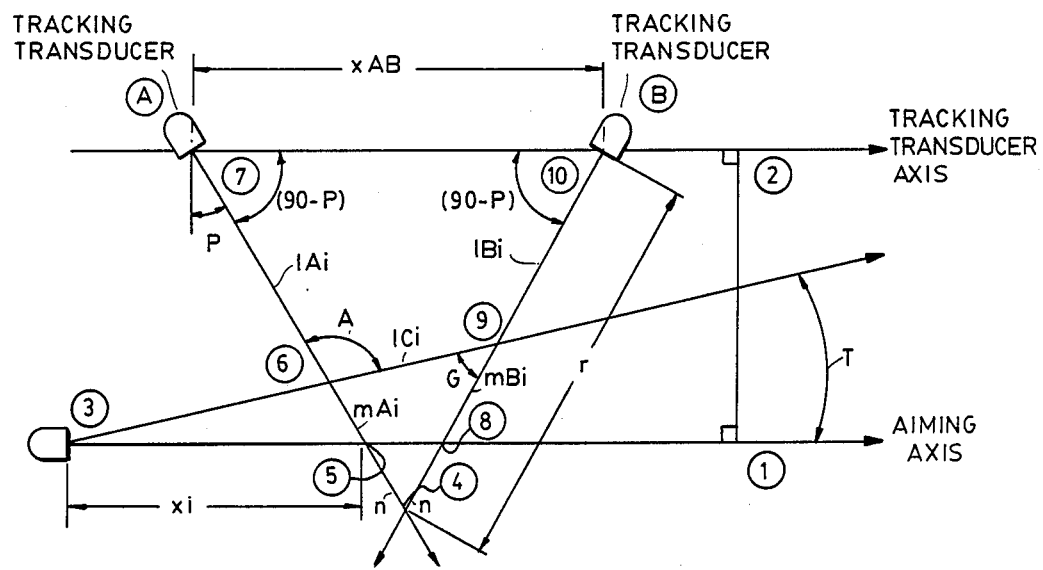
FIG. 3 is a geometric representation defining the variables used in the disclosure of the present invention.

The geometric and trigonometric variables used in the derivation of the equations necessary to practice the present invention are depicted in FIG. 3. These variables are defined as follows:

xAB = distance between tracking transducers A and B which are located at points 7 and 10 along the tracking transducer axis;

P = the angle between the tracking beam emitted from the left outer tracking transducer and an axis which is normal to the aiming axis of the tracked transducer;

$-P$ = the angle between the tracking beam emitted from the right outer tracking transducer and an axis which is normal to the aiming axis of the tracked transducer;

xi = distance from the tracked transducer lying at point 3 to the intersection of the aiming axis and the tracking transducer beam from tracking transducer A, point T = the angle between the tracked beam and the aiming axis;

lAi = the distance from point 6 to point 7;

lBi = the distance from point 9 to point 10;

lCi = the distance from point 6 to point 9;

mAi = the distance from point 5 to point 6; and mBi = the distance from point 8 to point 9.

n = distance from the intersection of the two outer tracking beams, point 4, to the intersection of each tracking beam with the aiming axis, points 5 and 8.

r = distance from the intersection of the two tracking beams, point 4, to each tracking transducer, points 7 and 10.

k = n/r; this is a measure of how far from the intersection of the tracking beams the tracked beam would be for an angle of misdirection, T, equal to 0.

A = an angle as depicted in FIG. 3.

G = an angle as depicted in FIG. 3.

Li = lBi + lCi − lAi = path difference in going from the tracked transducer to each of the tracking transducers.

We are interested in the behavior of Li as a function of the other parameters. Ultimately, we wish to obtain Li as a function of only T, P, k, xAB and xi. We will then use this expression for Li to obtain an equation for the speed of sound, C.

Still referring to FIG. 3, by applying the law of sines to the triangle formed by line segments between points 4, 7 and 10 it is apparent that $$r/\sin(90° - P) = xAB/\sin(180° - (90° - P) - (90° - P)) \quad (1).$$

In solving for r in equation (1) we obtain:

$$r = (xAB)\cos(P)/\sin(2P) \quad (2).$$

It can be seen from FIG. 3 that A is part of the triangle formed by the line segments between points 3, 5 and 6. From this relationship it is apparent that:

$$A + T + (90° - P) = 180° \quad (3).$$

Equation (3) is solved for A to obtain:

$$A = 90° + P - T \quad (4).$$

Similarly, by noting that G is part of the triangle formed by the line segments between points 3, 8 and 9, we obtain the following relationship:

$$G + T + (180° - (90° - P)) = 180° \qquad (5).$$

Equation (5) can be simplified to:

$$G = 90° - P - T \qquad (6)$$

lAi is defined as:

$$lAi = r - mAi - n \qquad (7).$$

By substituting the value of k, defined above, into equation (7), we obtain:

$$lAi = r - mAi - kr = (1 - k)r - mAi \qquad (8).$$

Similarly, for lBi we obtain:

$$lBi = r - (mBi + n) \qquad (9).$$

By noting that lCi is part of the triangle formed by the lined segments between points 4, 6 and 9 and by using the law of sines, we obtain:

$$lCi/\sin(180° - 2(90° - P)) = (n + mAi)/\sin(G) \qquad (10).$$

Equation (10) can be solved for lCi and simplified to yield:

$$lCi = (n + mAi)\sin(2P)/\sin(G) \qquad (11).$$

Next, we derive an expression for mAi. The law of sines is applied to the triangle formed by the line segments between points 3, 5 and 6 to obtain:

$$mAi/\sin(T) = xi/\sin(A) \qquad (12).$$

Equation (12) is solved for mAi to obtain:

$$mAi = xi \sin(T)/\sin \qquad (13).$$

A similar procedure is used to obtain mBi, by applying the law of sines to the triangle formed by the line segments between points 4, 6 and 9 to obtain:

$$(n + mBi)/\sin(180° - A) = (n + mAi)/\sin(G) \qquad (14).$$

Equation (14) can be reduced to:

$$mBi + n = (n + mAi)\sin(A)/\sin(G) \qquad (15).$$

Equation (15) is solved for mBi to yield:

$$mBi = (n + mAi)[\sin(A)/\sin(G)] - n \qquad (16).$$

In the following sequence of equations, expressions for lAi, lBi, and lCi are in terms of k, P, T, xAB, and xi. These equations will then be combined to obtain a general expression for Li. lAi can be written in the following form:

$$lAi = (1 - k)r - xi \sin(T)/\sin(A) \qquad (17).$$

By substituting equation (2) into equation (17), we obtain:

$$lAi = (1 - k)xAB[\cos(P)/\sin(2P)] - xi \sin(T)/\sin(A) \qquad (18).$$

lBi is defined by the following expression:

$$lBi = r - (n + mAi)\sin(A)/\sin(G) \qquad (19).$$

By substituting in the values of r, n, and mAi found in equations (2), (13) and the definition of variables, above, we obtain:

$$lBi = xAB[(\cos(P)/\sin(2P)] - [(k)xAB(\cos(P)/\sin(2P)) + xi(\sin(T)/\sin(A))] \sin(A)/\sin(G) \qquad (20).$$

By algebraic manipulation, equation (20) reduces to:

$$lBi = xAB[\cos(P)/\sin(2P)][1 - k \sin(A)/\sin(G)] - xi \sin(T)/\sin(G) \qquad (21).$$

Equation (21) can be simplified to yield:

$$lBi = xAB[\cos(P)/\sin(2P)][1 - k \sin(90° + P - T)/\sin(90° - P - T)] - xi \sin(T)/\sin(90° - P - T) \qquad (22).$$

lCi is defined by the following expression:

$$lCi = (n + mAi) \sin 2P/\sin(90° - P - T) \qquad (23).$$

By substitution of variables, as done above, equation (23) is written as:

$$lCi = [kr + xi \sin(T)/\sin(A)]\sin(2P)/\sin(90° - P - T) \qquad (24).$$

Equation (24) can be simplified to yield the following equation:

$$lCi = [(k)xAB(\cos(P)/\sin(2P) + xi \sin(T)/\sin(90° + P - T)][\sin(2P)/\sin(90° - P - T)] \qquad (25).$$

By further algebraic manipulation, equation (25) yields:

$$lCi = [(k)xAB(\cos(P)/\sin(2P)) + xi \sin(T)/\cos(T - P)][\sin(2P)/\cos(P + T)] \qquad (26).$$

As stated before:

$$Li = lBi + lCi - lAi \qquad (27).$$

By substituting the values of lAi, lBi, and lCi found in equations (18), (22), and (26), into equation (27) we obtain:

$$Li = xAB [\cos(P)/\sin(2P)] [1 - k \cos(T - P)/\cos(T + P)] - xi[\sin(T)/\cos(P + T)] + [(k)xAB(\cos(P)/\sin(2P)) + xi \sin(T)/\cos(T - P)] [\sin(2P)/\cos(P + T)] - (1 - k)xAB(\cos(P)/\sin(2P)) + xi \sin(T)/\cos(T - P). \qquad (28)$$

Equation (28) shows that Li is equal to a set of terms, which are functions of either xAB or xi, but not both. The coefficients of xi determine how Li changes with xi, and are a function only of the angles P and T. From equation (28), the coefficient of xi, Kxi, can be written as:

$$Kxi = -\sin(T)/\cos(P + T) + [\sin(T)/\cos(T - P)] \cdot [\sin(2P)/\cos(P + T)] + [\sin(T)/\cos(T - P)] \qquad (29).$$

Equation (29) can be reduced to:

$$Kxi = [\sin(T)][(-1/\cos(T + P)) + \sin(2P)/(\cos(T + P)\cos(T - P)) + 1/\cos(T - P)] \qquad (30).$$

Equation (30) can be algebraically simplified to:

$$Kxi = [\sin(T)][\sin(2P) + \cos(T+P) - \cos(T-P)] / [\cos(T+P)\cos(T-P)] \quad (31)$$

In some cases, it is reasonable to assume that T is a small angle. In these cases the following trigonometric assumptions are acceptable:

$$\sin(T) \simeq T \quad (32)$$

$$\cos(T) \simeq 1 \quad (33)$$

By substituting equations (32) and (33) as well as the following trigonometric law $$\cos(a \pm b) = \cos(a)\cos(b) \pm \sin(a)\sin(b) \quad (34)$$

into equation (31), we obtain:

$$Kxi = [\sin(T)] \, [-\cos(T)\cos(P) - \sin(T)\sin(P) + \sin(2P) + \cos(T)\cos(P) - \sin(T)\sin(P)] / [(\cos(T)\cos(P) - \sin(T)\sin(P))(\cos(T)\cos(P) + \sin(T)\sin(P))] \quad (35)$$

Equation (35) simplifies to:

$$Kxi = T[\sin(2P) - (2T)\sin(P)] / [\cos^2(P) - T^2 \sin^2(P)] \quad (36)$$

For values of P that are less than 60° and for values of T that are small, it is acceptable to neglect the second term in the denominator of equation (36). For these values, we obtain:

$$Kxi = T[\sin(2P) - (2T)\sin(P)] / \cos^2(P) \quad (37)$$

Thus, in cases where T is a small angle, the expression for Kxi shown in equation (37) yields accurate results. In a preferred embodiment of the present invention, equation (31) is used to define Kxi.

Equation (28) is an expression for the difference in distance from the tracked transducer to each of the tracking transducers. This difference in distance is proportionately related to the difference in arrival time for a pulse of ultrasound energy to travel from the tracked transducer to each of the tracking transducers. The differences in arrival times and distances are related by the speed of sound in the material.

The actual speed of sound, C, is related to the measured speed of sound as defined by the following relationship:

$$C = Kxi[\Delta xi / \Delta t] \quad (38)$$

where $\Delta xi$ and $\Delta t$ are measured distances and travel times.

Figure 5:
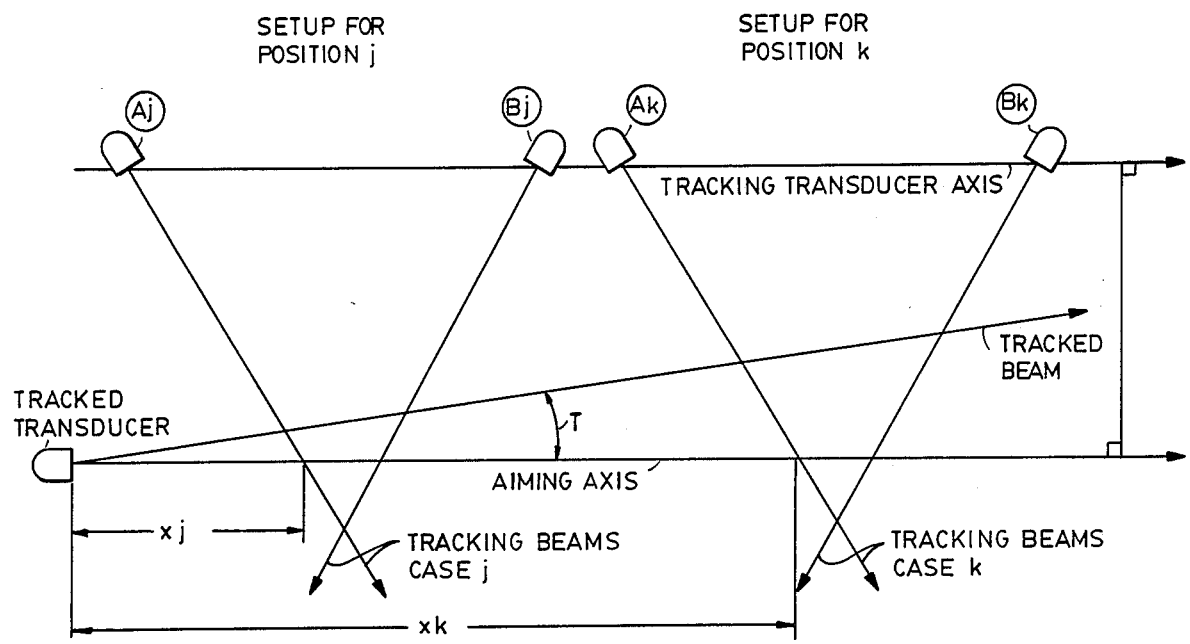
FIG. 5 is a geometric representation of a multiple tracking system with multiple pairs of transducers.

Referring to FIG. 5, the following relationship is evident:

$$Kxi(xj - xk)/C = (tjB - tjA) - (tkB - tkA) \quad (39)$$

where:

xj = the distance between the tracked transducer and the point of intersection between the aiming axis and the tracking beam emitted from tracking transducer A located at position j;

xk = the distance between the tracked transducer and the point of intersection between the aiming axis and the tracking beam emitted from transducer A located at position k;

tjA = the time required for ultrasound energy to travel from the tracked transducer to tracking transducer A located at position j;

tjB = the time required for ultrasound energy to travel from the tracked transducer to tracking transducer B located at position j.

The same rationale applies to the definitions of tkA and tkB. Dividing both sides of equation (39) by $(xj - xk)$, we obtain:

$$Kxi/C = [(tjB - tjA) - (tkB - tkA)] / (xj - xk) \quad (40)$$

Equation (40) is simplified to obtain:

$$Kxi/C = [(tjB - tkB)/(xj - xk)] - [(tjA - tkA)/(xj - xk)] \quad (41)$$

It is evident that the variables on the right side of equation (40) are written in terms of time/distance, the inverse of the speed of sound. Equation (41) can be simplified to yield:

$$Kxi/C = 1/CB - 1/CA \quad (42)$$

where CB is the speed of sound estimate for tracking transducer B, and CA is the speed of sound estimate for tracking transducer A. Kxi is a function of the angles T and P.

By substituting the value of Kxi defined by equation (31) into equation (42) we obtain:

$$\sin(T) \frac{\sin(2P) + \cos(T+P) - \cos(T-P)}{[\cos(T+P)][\cos(T-P)]} = \frac{C}{CB} - \frac{C}{CA} \quad (43)$$

Equation (43) defines one of the simultaneous equations which is used in the method of the present invention to solve for the speed of sound, C. The other simultaneous equation to be solved by the method of the present invention is the equation for the error factor resulting from misdirection of the tracked beam by an angle T. The following is a derivation of the error factor equation.

Figure 4:
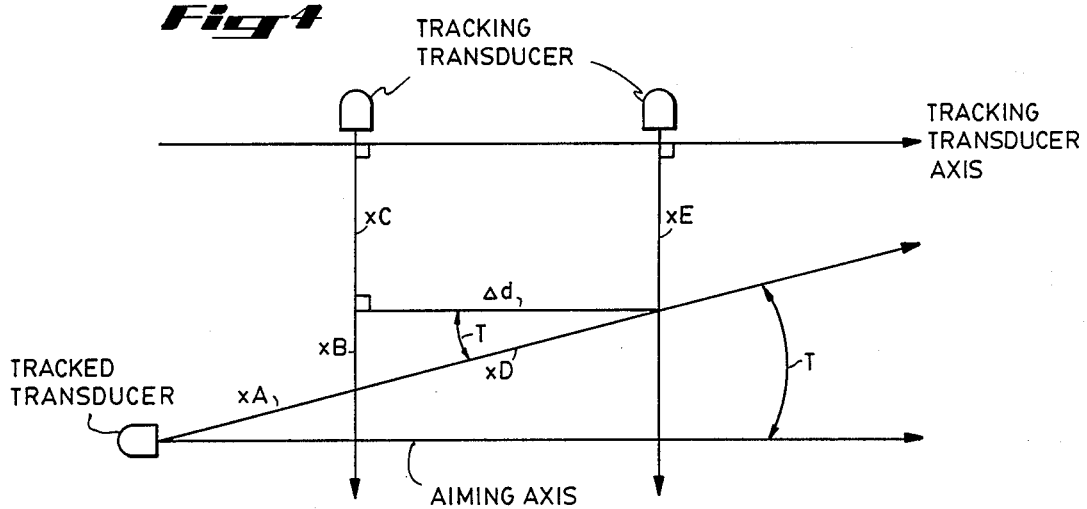
FIG. 4 is a geometric representation depicting the relationships defined in the derivation of the error factor resulting from misdirection of the tracked beam.

Referring to FIG. 4, a multi-transducer arrangement is depicted to determine the velocity of sound in vivo by the prior art method taught in U.S. Pat. No. 4,669,482. In FIG. 4 it can be seen that xE = xC. In this method, two tracking transducers are oriented along axes normal to the aiming axis of the tracked transducer. The tracked transducer beam is misdirected by an angle T. The difference in the distance from the tracked transducer to each of the tracking transducers, $\Delta l$, is defined by the following equation:

$$\Delta l = xD - xB \quad (44)$$

From established trigonometric relationships, xB and xD are defined as follows:

$$xB = \Delta d \tan(T); \quad (45)$$

$$xD = \Delta d / \cos(T) \quad (46)$$

Equations (45) and (46) are substituted into equation (44) to yield:

$$\Delta l = \Delta d[(1/\cos(T)) - \tan(T)] \quad (47)$$

Using well known trigonometric relationships, equation (47) reduces to:

$$\Delta l = \Delta d(1 - \sin(T))/\cos(T) \quad (48)$$

The actual speed of sound, C, is related to the difference in arrival times, $\Delta t$, and distances traveled, $\Delta l$, by the following relationship:

$$C\Delta t = \Delta l \quad (49)$$

By the method of the present invention, the speed of sound is estimated by measuring and recording the time required for ultrasound energy to travel from the tracked transducer to each of the tracking transducers. The experimentally determined speed of sound, CE is thus determined from the known distance between the tracking transducers, $\Delta d$, and time measured for sound to travel from the tracked transducer to each tracking transducer. Thus, CE is defined by the following relationship:

$$CE = \Delta d / \Delta t \quad (50)$$

By substituting equation (48) into equation (49) we obtain:

$$C = \frac{\Delta d}{\Delta t}[1 - \sin(t)]/\cos(T). \quad (51)$$

By substituting equation (50) into equation (51), we obtain:

$$C = CE[1 - \sin(T)]/\cos(T) \quad (52)$$

Equation (52) is the second simultaneous equation to be solved along with equation (31) by one method of the present invention to determine the speed of sound, C.

Now that the bases for the simultaneous equations employed in the method of the present invention have been set forth, the actual steps employed in practicing the preferred method of the present invention are as follows.

Figure 6:
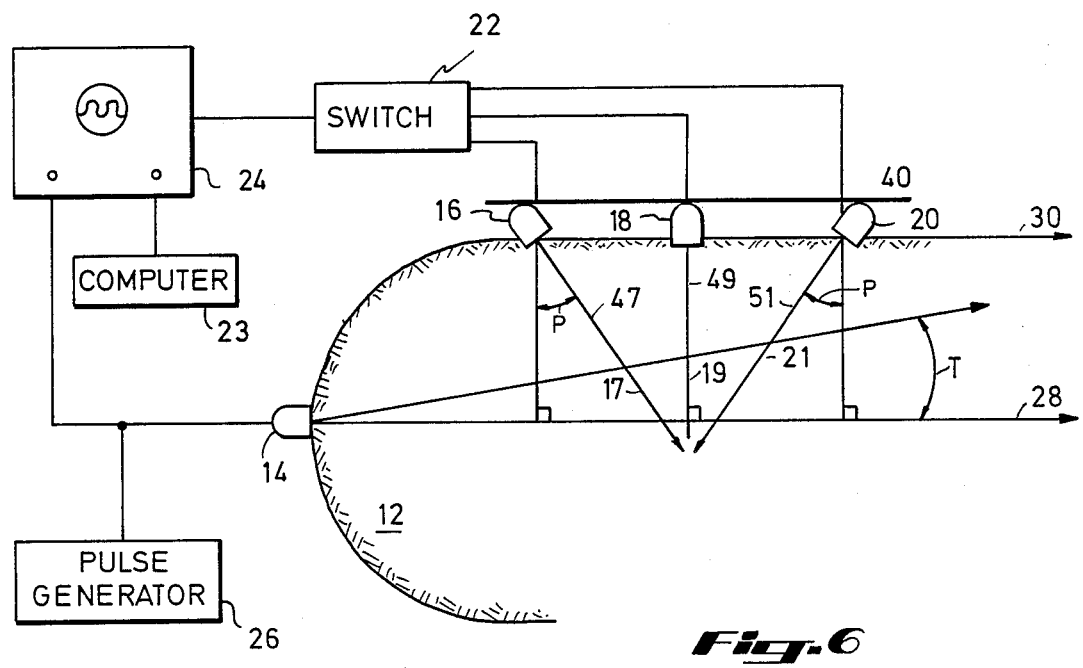
FIG. 6 is one embodiment of the present invention using three tracking transducers.

Referring to FIG. 6, a tracked ultrasound transducer 14 is applied to a target medium 12. Tracked transducer 14 is oriented along an aiming axis 28 in target medium 12.

A central tracking transducer 18 is applied to the outside of target medium 12 and oriented along an axis which is normal to aiming axis 28. Two outer tracking transducers 16 and 20 are applied to the outer surface of target medium 12 on the left and right sides of central tracking transducer 18, respectively. Tracking transducers 16, 18 and 20 are aligned along tracking transducer axis 30 which is parallel to aiming axis 28 and which lies in the same two dimensional plane as aiming axis 28. Outer tracking transducers 16 and 20 are oriented at angles P and −P, respectively, toward central tracking transducer 18 from an axis normal to aiming axis 28. Tracking transducers 16, 18 and 20 are connected together via an attachment arm 40.

A pulse generator 26 is used to generate a tracked transducer beam from tracked transducer 14. The tracked transducer beam is misdirected by an angle T from aiming axis 28 along axis 32. At point 17 on axis 32 ultrasound energy is scattered by scatterers along the tracked beam along axis 47 to left tracking transducer 16. At point 19, ultrasound energy is scattered from the tracked beam along axis 49 to central tracking transducer 18. At point 21 ultrasound energy is scattered from the tracked beam along axis 51 to right tracking transducer 20.

Transducers 14, 16, 18 and 20 are coupled electronically to a pulse generator 26 and an energy measuring and timing device 24, such as an oscilloscope. Data measured by the measuring and timing device can be stored in a computer 23 which is electronically coupled to measuring and timing device 24. Tracking transducers 16, 18 and 20 are electronically coupled to a switch 22. Switch 22 is coupled electronically to measuring and timing device 24 such that measuring and timing device 24 will selectively record time and pulse measurements for the tracking transducer selected by the placement of switch 22.

Tracking transducers 16, 18 and 20 each receive ultrasound energy from the tracked beam. Switch 22 is selectively aligned such that oscilloscope 24 can record the time required for ultrasound energy to travel from tracked transducer 14 to each tracking transducer 16, 18 and 20.

Once travel time measurements are obtained for each of tracking transducers 16, 18 and 20, these tracking transducers are relocated along tracking transducer axis 30 a distance $\Delta x$ in the same direction as previously translated from their present location. This transducer relocation is accomplished by moving attachment arm 40 a distance $\Delta x$ in the direction of translation. Another beam of ultrasound energy is emitted by tracked transducer 14 and the time required for ultrasound energy to travel from tracked transducer 14 to tracking transducers 16, 18 and 20 is again recorded using oscilloscope 24. This relocation and time measurement sequence is repeated until a plurality of data sets for travel time at each location for tracking transducers 16, 18 and 20 are obtained.

From the plurality of data sets, a functional relationship between travel time and location is determined for each of tracking transducers 16, 18 and 20. In a preferred embodiment, this functional relationship is determined by plotting the plurality of data sets on a graph where location is plotted on a vertical Y axis versus time plotted on a horizontal X axis for each of tracking transducers 16, 18 and 20. The speed of sound between the tracked transducer and each of tracking transducers 16, 18 and 20, respectively denoted by CA, CE, and CB is determined from the plot of the data pairs obtained for each tracking transducer. In a preferred embodiment, the speed of sound for each tracking transducer is determined by fitting a line determined by a regression technique to each plot of data pairs. The slope of the fitted line is then calculated to yield the speed of sound for each tracking transducer. These calculations are carried out by the computer 23.

It is also possible to plot location on the X axis and time on the Y axis and determine velocity from the reciprocal of the slope of a line fitted to the data via a regression technique.

Once CB, CA, and CE are determined from the data pairs, the following two equations:

$$C = CE[1 - \sin(T)]/\cos(T); \text{ and}$$

$$\sin(T)\frac{\sin(2P) + \cos(T+P) - \cos(T-P)}{[\cos(T+P)][\cos(T-P)]} = \frac{C}{CB} - \frac{C}{CA}$$

are solved numerically to determine the speed of sound, C. In a preferred embodiment, the numerical method used to simultaneously solve the above two equations is an iterative numerical method. The method is carried out by computer 23.

Figure 7:
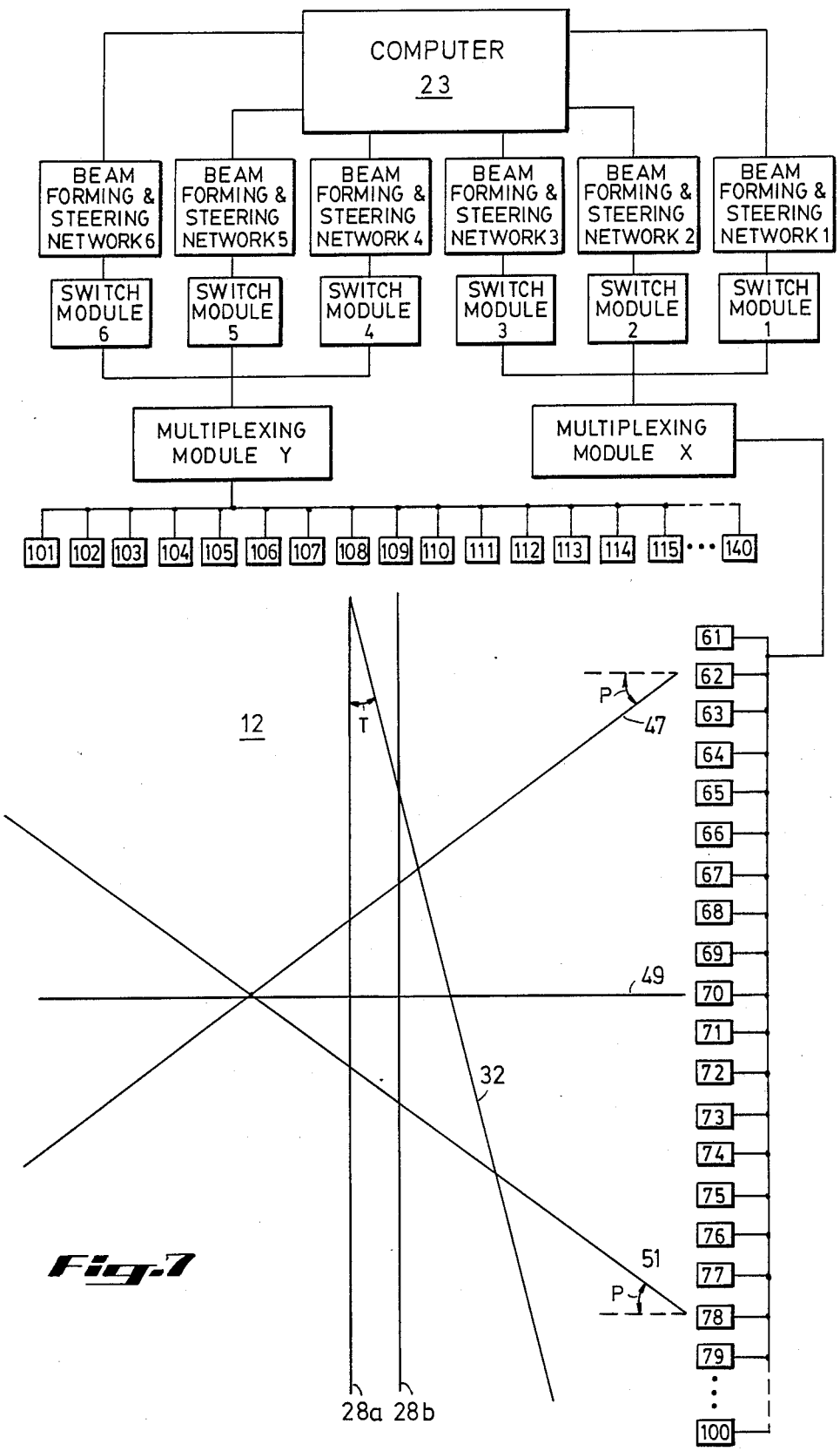
FIG. 7 is another embodiment of the present invention using a multiplicity of tracking and tracked transducers in phased arrays.

Another embodiment of the present invention using multiple tracking transducers is shown in FIG. 7. The configuration shown in FIG. 7 can be operated in two different modes. In the first mode, transducers 61-100 operate as tracking transducers in order to calculate the speed of sound along a tracked beam emitted from tracked transducers 101-140. In this configuration, the aiming axis of the tracked beam is coincident with or parallel to aiming axis 28a.

In the second mode of operation for the configuration depicted in FIG. 7, the tracking and tracked functions of the transducers are reversed. Transducers 101-140 are operated as tracking transducers to measure the speed of sound along a tracked beam emitted by tracked transducers 61-100. In this mode of operation the aiming axis is coincident with or parallel to axis 49. Thus, the configuration depicted in FIG. 7 can be used to measure the speed of sound along two sets of multiple tracked beams oriented perpendicularly to each other.

The embodiment depicted in FIG. 7 permits the determination of sound velocity using a multi-beam system in which physical relocation of the transducers is not required. Movement of the transducers is eliminated by the use of multiplexing circuitry and beam forming and steering networks. The number of tracking and tracked transducers represented in FIG. 7 is merely illustrative Systems using more or less tracking and tracked transducers in a similar configuration are acceptable to practice the present invention.

The transducers depicted in FIG. 7 can be operated in phased arrays using methods well known in the medical imaging arts. A typical phase array system is described in "Cardiac Imaging Using A Phased Array Ultrasound System" by Olaf T. Van Ramm and Federick L. Thurstone, *Circulation*, Volume 53, No. 2, February 1976. In a phased array system, multiple transducer elements are operated jointly to produce or receive a single signal. In the embodiment depicted in FIG. 7, each phased array consists of three transducers or transducer elements. The use of three transducer elements per phased array is merely illustrative.

Transducers 61-100 are coupled electronically to multiplexing module X. Multiplexing module X is coupled electronically to switch modules 1-3. Beam forming and steering networks 1-3 are coupled electronically to switch modules 1-3, respectively. This configuration permits the actuation of selected groups of transducers by each beam forming and steering network by manipulation of the respective switch module.

In the initial set of readings to be taken, transducer elements 61-63 constitute the phased array which functions as the left outer tracking transducers. Transducer elements 69-71 constitute the phased array which functions as the central tracking transducer. Transducer elements 77-79 constitute the phased array which functions as the right outer tracking transducer. Transducer elements 107-109 constitute the phased array which will function as the tracked transducer.

Processing of the phased array signals and orientation lf the outer tracking transducers at angles P and —P are accomplished by the beam forming and steering networks. The beam forming and steering networks are operated such that the transducer elements electronically coupled to the beam forming and steering network ca transmit and receive ultrasound energy at a desired angle, such as —P or P. This eliminates the need to physically orient the outer transducers at an angle P or —P from an axis normal to aiming axis 28a. The beam forming and steering networks also provide a pulse generation function for all of the transducers.

In this mode of operation, only one switch module and one beam forming and steering network set is needed to be electronically coupled to transducers 101-140. For discussion purposes it will be assumed that beam forming and steering network 4 is used to generate a tracked transducer beam from tracked transducer array 107-109. The tracked transducer beam, upon entering the target medium is misdirected by an angle T from aiming axis 28a along axis 32.

Tracking transducers 61-63, 69-71, and 77-79, each receive ultrasound energy from the tracked beam. The time required for ultrasound energy to travel from the tracked transducer array to the three tracking transducer arrays is measured and recorded by computer 23.

Once travel time measurements are obtained for each tracking transducer phased array, switch modules 1-3 are manipulated to change the individual transducer elements which make up each phased array. This is the physical equivalent of relocating the transducers in the phased array. In the present embodiment, the transducer elements constituting the left outer tracking transducer are switched from 61-63 to 62-64. The transducer elements constituting the central tracking transducer are switched from 69-71 to 70-72. The transducer elements constituting the right outer tracking transducer are switched from 77-79 to 78-80. Travel times are again measured and stored in computer 23 as before. Thus, each phased array is shifted a distance $\Delta x$ in the direction of translation. This switching process is repeated to obtain a multiplicity of data sets along the direction of translation of transducer elements 61-100.

From the plurality of data sets, the data is analyzed and the simultaneous equations described above are solved using a numerical method to determine the speed of sound, C.

The accuracy of the sound measurement obtained using the configuration shown in FIG. 7 can be increased by taking sound measurements along more than one tracked beam axis. This is accomplished by switching the transducer elements which constitute the tracked transducer via switch module 4. Thus, the transducer elements which make up the tracked transducer can be switched from 107-109 to 108-110 to produce aiming axis 28b parallel to previous aiming axis 28a. The measurement and data analysis sequence described above can then be repeated for the new tracked beam. This sequence of measurements can be taken for a multiplicity of tracked beams produced by a multiplicity of phased array transducers in the direction of translation of transducer elements 101-140. The average sound velocity can then be calculated from the sound velocity determined for each tracked beam axis.

Although the invention has been described with a certain degree of particularity, it is understood that the description of the preferred embodiment has been only by way of example. Numerous modifications and variations of the embodiments discussed herein are suitable for practicing the present invention.

What is claimed is:

1. A method of correcting for angle error in sound velocity estimations in a target medium using ultrasound transducers comprising the steps of:
   (a) applying a tracked ultrasound transducer oriented along an aiming axis to the outer surface of a target medium;
   (b) applying a central tracking transducer oriented along an axis normal to the aiming axis of said tracked transducer to the outer surface of a target medium;
   (c) applying a left and a right outer tracking transducer to the outer surface of a target medium, each of said outer tracking transducers placed on an opposite side of said central tracking transducer forming a tracking transducer axis with said central tracking transducer, said tracking transducer axis being parallel to said aiming axis and said left and right outer tracking transducers oriented at angles P and −P, respectively, from an axis normal to the aiming axis toward said central tracking transducer;
   (d) employing a means for measuring the energy and travel time of signals produced by said ultrasound transducers;
   (e) generating a tracked beam from said tracked ultrasound transducer which is misdirected at an angle T from said aiming axis;
   (f) receiving ultrasound energy scattered from scatterers along said tracked beam to each of said tracking transducers;
   (g) measuring the travel time required for ultrasound energy to travel from the tracked transducer to each of said tracking transducers;
   (h) recording each of said measured travel times;
   (i) relocating each of said tracking transducers a distance $\Delta x$ from its present location in the same direction along said tracking transducer axis;
   (j) repeating steps (d)–(i) to obtain a plurality of data sets for travel time at each location for each of said tracking transducers;
   (k) plotting the plurality of data sets obtained in step (j) for each of said tracking transducers;
   (l) fitting a line to each of the plots made in step (k);
   (m) estimating the speed of sound along the tracked beam by calculating the slope of each of the fitted lines obtained in step (l);
   (n) solving the following two equations, labeled (1) and (2), for the speed of sound, C:

$$C = CE\,[1 - \sin(T)]/\cos(T); \text{ and} \quad (1)$$

$$\sin(T)\,\frac{\sin(2P) + \cos(T + P) - \cos(T - P)}{[\cos(T + P)]\,[\cos(T - P)]} = \frac{C}{CB} - \frac{C}{CA} \quad (2)$$

where
   CE = the speed of sound obtained in step (m) for the central tracking transducer;
   T = the angle of misdirection which the tracked beam undergoes in step (d);
   P = the angle between the axis along which the left outer tracking transducers is aimed and an axis normal to the aiming axis;
   CB = the speed of sound obtained in step (m) for one of said outer tracking transducers; and
   CA = the speed of sound obtained in step (m) for the other outer tracking transducer.

2. The method of claim 1 wherein the plotting of the plurality of data sets obtained in step (j) for each of said tracking transducers is accomplished by plotting location on a vertical Y axis versus travel time on a horizontal X axis for each of said tracking transducers.

3. The method of claim 1 wherein the simultaneous solving of the two equations shown in step (n) is accomplished with a computer using an iterative numerical method.

4. The method of claim 1 wherein relocating each of said tracking transducers a distance $\Delta x$ from its present location is accomplished by moving an attachment arm fastened to each of the tracking transducers a distance $\Delta x$.

5. A method for calculating the in vivo sound velocity in a target medium using multiple ultrasound transducers comprising the steps of:
   (a) applying a tracked ultrasound transducer oriented along an aiming axis to the outer surface of a target medium;
   (b) applying a central tracking transducer oriented along an axis normal to the aiming axis of said tracked transducer to the outer surface of a target medium;
   (c) applying a right outer tracking transducer on the right side of said central tracking transducer, said right tracking transducer and said central tracking transducer forming a tracking transducer axis parallel to said aiming axis, said right tracking transducer being oriented at an angle −P toward said central tracking transducer from an axis normal to the aiming axis;
   (d) applying a left outer tracking transducer on the left side of said central tracking transducer, said left outer tracking transducer, said right outer tracking transducer and said central tracking transducer forming a tracking transducer axis parallel to said aiming axis, said left tracking transducer being oriented at an angle P toward said central tracking transducer from an axis normal to tee aiming axis;
   (e) connecting said tracked transducer and said tracking transducers electronically to an energy measuring and timing device;
   (f) generating a tracked beam from said tracked ultrasound transducer which is misdirected at an angle T from said aiming axis;
   (g) receiving ultrasound energy scattered from scatters along said tracked beam to each of said tracking transducers;
   (h) recording the travel time required for ultrasound energy to travel from the tracked transducer to each of said tracking transducers;
   (i) relocating each of said tracking transducers a distance $\Delta x$ from its present location in the same direction along said tracking transducer axis;
   (j) repeating steps (f)–(i) to obtain a plurality of data sets for travel time at each location for each of said tracking transducers;
   (k) determining the functional relationship between travel time and location from the plurality of data sets obtained for each of said tracking transducers in step (j);
   (l) estimating the speed of sound along the tracked beam from the functional relationship obtained in step (k) for each of said tracking transducers;
   (m) solving the following two equations, labeled (1) and (2), for the speed of sound, C:

$$C = CE\,[1 - \sin(T)]/\cos(T); \text{ and} \quad (1)$$

-continued $$\sin(T) \frac{\sin(2P) + \cos(T + P) - \cos(T - P)}{[\cos(T + P)][\cos(T - P)]} = \frac{C}{CB} - \frac{C}{CA} \quad (2)$$

where
CE = the speed of sound obtained in step (m) for the central tracking transducer;
T = the angle of misdirection which the tracked beam undergoes in step (d);
P = the angle between the axis along which the left outer tracking transducer is aimed and an axis normal to the aiming axis;
CB = the speed of sound obtained in step (l) for said right outer tracking transducer; and
CA = the speed of sound obtained in step (l) for said right outer tracking transducer.

6. The method of claim 5 wherein said tracked transducer and said tracking transducers are connected electronically to a computer.

7. The method of claim 5 wherein determining the functional relationship between travel time and location from the plurality of data sets obtained for each of the tracking transducers is accomplished by fitting a line to the data sets using a linear regression technique.

8. The method of claim 5 wherein said recording the travel time required for ultrasound energy to travel from the tracked transducer to each of the tracking transducers is accomplished for each tracking transducer by selecting a switch position on a switch electronically coupled to each of said tracking transducers and the pulse recording apparatus.

9. A method for calculating the in vivo sound velocity in a target medium using multiple ultrasound transducers comprising the steps of:
(a) applying a tracked transducer oriented along an aiming axis to the outer surface of a target medium;
(b) applying a multiplicity of tracking transducers aligned along a tracking transducer axis which is parallel to the aiming axis;
(c) electronically coupling each of said tracking transducers to a switch mechanism;
(d) electronically coupling the switch mechanism to a measuring and timing device;
(e) manipulating the switch mechanism to selectively couple three groups of tracking transducers to the measuring and timing device, said groups comprising a left outer tracking transducer oriented at an angle P from an axis normal to the aiming axis, a central tracking transducer oriented along an axis normal to the aiming axis, and a right outer tracking transducer oriented at an angle −P from an axis normal to the aiming axis;
(f) generating a tracked beam from the tracked ultrasound transducer, said tracked beam being misdirected at an angle T from the aiming axis;
(g) receiving ultrasound energy scattered from scatterers along said tracked beam to each of the tracking transducer groups coupled to the measuring and timing device;
(h) recording the travel time required for ultrasound energy to travel from the tracked transducer to each of the tracking transducer groups coupled to the measuring and timing device;
(i) manipulating the switch mechanism such that the measuring and timing device is coupled to three new groups of tracking transducers, each of said new groups of tracking transducers having shifted a distance Δx in the direction of translation from the position of the group of tracking transducers to which the measuring and timing device was coupled before the switch manipulation;
(j) repeating steps (f)-(i) to obtain a plurality of data sets for travel time at each location for each of the tracking transducer groups;
(k) determining the functional relationship between travel time and location from the plurality of data sets obtained for each of said tracking transducers in step (j);
(l) estimating the speed of sound along the tracked beam from the functional relationship obtained in step (k) for each of said tracking transducers;
(m) solving the following two equations, labeled (1) and (2), for the speed of sound, C:

$$C = CE [1 - \sin(T)]/\cos(T); \text{ and} \quad (1)$$

$$\sin(T) \frac{\sin(2P) + \cos(T + P) - \cos(T - P)}{[\cos(T + P)][\cos(T - P)]} = \frac{C}{CB} - \frac{C}{CA} \quad (2)$$

where
CE = the speed of sound obtained in step (m) for the central tracking transducer;
T = the angle of misdirection which the tracked beam undergoes in step (d);
P = the angle between the axis along which the left outer tracking transducer is aimed and an axis normal to the aiming axis;
CB = the speed of sound obtained in step (l) for said right outer tracking transducer; and
CA = the speed of sound obtained in step (l) for said right outer tracking transducer.

10. The method of claim 9 wherein each tracking transducer group comprises a single tracking transducer.

11. The method of claim 9 wherein each tracking transducer group comprises a phased array made up of a multiplicity of transducer elements.

12. The method of claim 9 wherein the multiplicity of tracking transducers are electronically coupled to a switch mechanism via a multiplexing module.

13. The method of claim 11 wherein phased array circuitry is used to orient the right and left outer tracking transducers at angles −P and P, respectively.

14. A method for calculating the in vivo sound velocity in a target medium using multiple ultrasound transducer elements comprising the steps of:
(a) applying a multiplicity of tracked ultrasound transducer elements oriented along an aiming axis to the outer surface of the target medium;
(b) applying a multiplicity of tracking transducer elements aligned along a tracking transducer axis which is parallel to the aiming axis;
(c) electronically coupling each of said tracked transducer elements to a first multiplexing module;
(d) electronically coupling each of said tracking transducer elements to a second multiplexing module;
(e) electronically coupling the first multiplexing module to at least one tracked transducer switch module;
(f) electronically coupling the second multiplexing module to three switch modules, said three switch modules to be known as the left switch module, the central switch module, and the right switch module;

(g) electronically coupling a beam forming and steering network to each of said switch modules;

(h) electronically coupling each beam forming and steering network to a computer.

(i) manipulating the central switch module such that a central group of tracking transducer elements operated in phased array are electronically coupled to the beam forming and steering network which is electronically coupled to the central switch module;

(j) manipulating the right switch module such that a group of transducer elements located to the right of the group of transducer elements electronically coupled to the central switch module are operated in phased array and electronically coupled to the beam forming and steering network which is electronically coupled to the right switch module;

(k) manipulating the left switch module such that a group of transducer elements located to the left of the group of transducer elements electronically coupled to the central switch module are operated in phased array and electronically coupled to the beam forming and steering network which is electronically coupled to the left switch module;

(l) operating the beam forming and steering network coupled to the left switch module such that the transducer elements operated in phased array and coupled to the left switch module transmit and receive ultrasound energy oriented at an angle P from an axis normal to the aiming axis;

(m) operating the beam forming and steering network coupled to the right switch module such that the transducer elements operated in phased array and coupled to the right switch module transmit and receive ultrasound energy oriented at an angle $-P$ from an axis normal to the aiming axis;

(n) operating the beam forming and steering network coupled to the central switch module such that the transducer elements operated in phased array and coupled to the central switch module transmit and receive ultrasound energy oriented at an angle normal to the aiming axis;

(o) generating a tracked beam via the beam forming and steering network electronically coupled to the tracked transducer switch module, said tracked beam being misdirected at an angle T from the aiming axis;

(p) receiving ultrasound energy scattered from scatterers along said tracked beam to each of the transducer elements operated in phased array coupled to the beam forming and steering networks;

(q) recording the travel time required for ultrasound energy to travel from the tracked transducer elements operated in phased array to each of the tracking transducer elements operated in phased array and coupled to the computer;

(r) manipulating the left switch module, the central switch module and the right switch module such that the computer and the beam forming and steering networks electronically coupled to each of said switch modules is now coupled to a new group of transducer elements which has shifted a distance $\Delta x$ in the direction of translation;

(s) repeating steps (o)–(r) to obtain a plurality of data sets for travel time at each location for each of the tracking transducer element phased arrays;

(t) determining the functional relationship between travel and location from the plurality of data sets obtained for each of said tracking transducers in step (s);

(u) estimating the speed of sound along the tracked beam from the functional relationship obtain in step (t) for each of said tracking transducers;

(v) solving the following two equations, labeled (1) and (2) for the speed of sound, C:

$$C = CE\,[1 - \sin(T)]/\cos(T); \text{ and} \qquad (1)$$

$$\sin(T)\frac{\sin(2P) + \cos(T+P) - \cos(T-P)}{[\cos(T+P)][\cos(T-P)]} = \frac{C}{CB} - \frac{C}{CA} \qquad (2)$$

where
CE = the speed of sound obtained in step (m) for the central tracking transducer;
T = the angle of misdirection which the tracked beam undergoes in step (d);
P = the angle between the axis along which the left outer tracking transducer is aimed and an axis normal to the aiming axis;
CB = the speed of sound obtained in step (l) for said right outer tracking transducer; and
CA = the speed of sound obtained in step (l) for said right outer tracking transducer.

15. The method of claim 14 further comprising:

(a) manipulating the tracked transducer switch module such that the group of transducer elements operated in phased array which is electronically coupled to this switch module is translated a distance $\Delta x$ in the direction of translation from its prior location;

(b) repeating steps (o)–(v) of claim 14 for the new tracked beam axis;

(c) repeating steps (a)–(b) for a multiplicity of tracked beam axes;

(d) calculating the average sound velocity from the sound velocity calculated for each tracked beam axis.

* * * * *